United States Patent
Rothenwaender et al.

(10) Patent No.: US 8,500,447 B2
(45) Date of Patent: Aug. 6, 2013

(54) MEDICAL HANDPIECE WITH PULSED ILLUMINATION

(75) Inventors: Michael Rothenwaender, Lamprechtshausen (AT); Christoph Kment, Vienna (AT); Juergen Koelndorfer, Vienna (AT); Herbert Weissenboeck, Feistritz (AT); Martin Milojkovic, Vienna (AT)

(73) Assignee: W&H Dentalwerk Bürmoos GmbH, Bürmoos (AT)

(*) Notice: Subject to any disclaimer, the term of this patent is extended or adjusted under 35 U.S.C. 154(b) by 285 days.

(21) Appl. No.: 12/577,068

(22) Filed: Oct. 9, 2009

(65) Prior Publication Data

US 2010/0092908 A1    Apr. 15, 2010

(30) Foreign Application Priority Data

Oct. 10, 2008 (EP) .................................. 08017761

(51) Int. Cl.
*A61C 1/00* (2006.01)
(52) U.S. Cl.
USPC .................... 433/29; 433/82; 433/84; 433/85
(58) Field of Classification Search
USPC ......... 433/29, 80, 31, 133, 82, 84, 85; 606/2, 606/3, 245, 246; 356/22–24; 315/246; 73/466
See application file for complete search history.

(56) References Cited

U.S. PATENT DOCUMENTS

| | | | | | |
|---|---|---|---|---|---|
| 3,614,414 | A | * | 10/1971 | Gores | 362/573 |
| 4,020,556 | A | * | 5/1977 | Sotman | 433/29 |
| 4,171,572 | A | * | 10/1979 | Nash | 433/29 |
| 4,208,579 | A | * | 6/1980 | Scrivo et al. | 250/227.22 |
| 4,341,518 | A | * | 7/1982 | Wallace | 433/29 |
| 4,477,252 | A | * | 10/1984 | Lieb et al. | 433/29 |
| 4,498,868 | A | * | 2/1985 | Schuss | 433/29 |
| 4,553,938 | A | * | 11/1985 | Olsen | 433/126 |
| 4,578,033 | A | * | 3/1986 | Mossle et al. | 433/29 |
| 4,790,751 | A | * | 12/1988 | Reinhardt et al. | 433/29 |
| 4,826,431 | A | * | 5/1989 | Fujimura et al. | 433/29 |
| 4,872,837 | A | * | 10/1989 | Issalene et al. | 433/29 |

(Continued)

FOREIGN PATENT DOCUMENTS

| | | |
|---|---|---|
| DE | 19511262 | 8/1996 |
| JP | 4-503320 | 6/1992 |
| JP | 8-154952 | 6/1996 |

OTHER PUBLICATIONS

Search Report dated Mar. 30, 2009, from European Patent Application No. EP 08017761, filed Oct. 10, 2008.

*Primary Examiner* — Cris L Rodriguez
*Assistant Examiner* — Matthew Saunders
(74) *Attorney, Agent, or Firm* — Klarquist Sparkman, LLP

(57) ABSTRACT

Medical treatment devices, such as dental treatment devices, include at least a drive unit for driving a tool configured to act on a treatment site, a light-emitting device and a cooling media dispensing device for dispensing at least one cooling medium onto a tool and/or a treatment site. The device can be controlled, such as with a controller, to substantially alternatingly operate the light-emitting device and the dispensing device, thereby intermittently illuminating the tool and/or the treatment site and dispensing cooling medium toward the tool and/or the treatment site, respectively, which provides a user with an improved view of the tool, the treatment site, or both.

22 Claims, 1 Drawing Sheet

U.S. PATENT DOCUMENTS

| | | | | |
|---|---|---|---|---|
| 4,886,455 A * | 12/1989 | Lohn | | 433/80 |
| 4,902,225 A * | 2/1990 | Lohn | | 433/80 |
| 4,940,411 A * | 7/1990 | Vassiliadis et al. | | 433/215 |
| 4,968,249 A * | 11/1990 | Lohn | | 433/80 |
| 4,975,058 A * | 12/1990 | Woodward | | 433/126 |
| 5,049,070 A * | 9/1991 | Ademovic | | 433/29 |
| 5,082,443 A * | 1/1992 | Lohn | | 433/80 |
| 5,092,864 A * | 3/1992 | Hayes et al. | | 606/10 |
| 5,096,418 A * | 3/1992 | Coss | | 433/29 |
| 5,115,307 A * | 5/1992 | Cooper et al. | | 348/66 |
| 5,145,370 A * | 9/1992 | Woodward | | 433/126 |
| 5,147,203 A * | 9/1992 | Seidenberg | | 433/29 |
| 5,178,536 A * | 1/1993 | Werly et al. | | 433/29 |
| 5,251,025 A * | 10/1993 | Cooper et al. | | 348/66 |
| 5,267,856 A * | 12/1993 | Wolbarsht et al. | | 433/29 |
| 5,267,857 A * | 12/1993 | Sickler | | 433/29 |
| 5,290,168 A * | 3/1994 | Cooper et al. | | 433/29 |
| 5,308,242 A * | 5/1994 | McLaughlin et al. | | 433/114 |
| 5,342,196 A * | 8/1994 | Van Hale | | 433/82 |
| 5,388,988 A * | 2/1995 | Goisser et al. | | 433/29 |
| 5,409,376 A * | 4/1995 | Murphy | | 433/29 |
| 5,429,502 A * | 7/1995 | Cooper et al. | | 433/29 |
| 5,593,304 A * | 1/1997 | Ram | | 433/82 |
| 5,634,790 A * | 6/1997 | Pathmanabhan et al. | | 433/29 |
| 5,636,983 A * | 6/1997 | Shoji et al. | | 433/29 |
| 5,647,745 A * | 7/1997 | Badoz | | 433/126 |
| 5,669,769 A * | 9/1997 | Disel | | 433/29 |
| 5,683,246 A * | 11/1997 | Coss et al. | | 433/29 |
| 5,733,120 A * | 3/1998 | Yao et al. | | 433/132 |
| 5,772,436 A * | 6/1998 | Matsui et al. | | 433/126 |
| 5,785,521 A * | 7/1998 | Rizoiu et al. | | 433/29 |
| 5,814,040 A * | 9/1998 | Nelson et al. | | 606/9 |
| 5,833,456 A * | 11/1998 | Davis et al. | | 433/29 |
| 5,833,684 A * | 11/1998 | Franetzki | | 606/17 |
| 5,846,080 A * | 12/1998 | Schneider | | 433/215 |
| 5,899,692 A * | 5/1999 | Davis et al. | | 433/80 |
| 5,968,034 A * | 10/1999 | Fullmer et al. | | 606/9 |
| 5,968,037 A * | 10/1999 | Rizoiu et al. | | 606/13 |
| 6,083,218 A * | 7/2000 | Chou | | 606/10 |
| 6,102,695 A * | 8/2000 | Rosenstatter | | 433/29 |
| 6,149,430 A * | 11/2000 | Nemetz et al. | | 433/132 |
| 6,156,030 A * | 12/2000 | Neev | | 606/10 |
| 6,186,784 B1 * | 2/2001 | Bailey | | 433/126 |
| 6,217,328 B1 * | 4/2001 | Oliver | | 433/80 |
| 6,247,929 B1 * | 6/2001 | Bachman et al. | | 433/80 |
| 6,270,342 B1 * | 8/2001 | Neuberger et al. | | 433/29 |
| 6,305,934 B1 * | 10/2001 | Hatley, Jr. | | 433/80 |
| 6,315,565 B1 * | 11/2001 | Slotke et al. | | 433/216 |
| 6,419,996 B2 * | 7/2002 | Mueller et al. | | 427/554 |
| 6,468,076 B2 * | 10/2002 | Kawamura | | 433/29 |
| 6,619,954 B2 * | 9/2003 | Cheney et al. | | 433/29 |
| 6,663,386 B1 * | 12/2003 | Moelsgaard | | 433/29 |
| 6,960,340 B2 * | 11/2005 | Rowe et al. | | 424/78.08 |
| 6,991,736 B2 * | 1/2006 | Downs | | 210/764 |
| 7,008,224 B1 * | 3/2006 | Browning et al. | | 433/104 |
| 7,108,505 B2 * | 9/2006 | Cheney et al. | | 433/29 |
| 7,217,254 B2 * | 5/2007 | Kirwan et al. | | 604/82 |
| 7,267,672 B2 * | 9/2007 | Altshuler et al. | | 606/2 |
| 7,284,981 B2 * | 10/2007 | Schmid et al. | | 433/29 |
| 7,320,594 B1 * | 1/2008 | Rizoiu et al. | | 433/29 |
| 2001/0012605 A1 * | 8/2001 | Kawamura | | 433/29 |
| 2007/0265605 A1 * | 11/2007 | Vaynberg et al. | | 606/13 |
| 2008/0032251 A1 * | 2/2008 | Chou | | 433/29 |
| 2008/0131835 A1 * | 6/2008 | Schatz et al. | | 433/29 |
| 2009/0042171 A1 * | 2/2009 | Rizoiu et al. | | 433/224 |

\* cited by examiner

MEDICAL HANDPIECE WITH PULSED ILLUMINATION

CROSS REFERENCE TO RELATED APPLICATION

The present application claims priority from and benefit of pending European Patent Application No. 08017761 filed Oct. 10, 2008, which is incorporated herein by reference.

FIELD

The present application relates to medical treatment devices, and more particularly, but not exclusively, to dental treatment devices with a light-emitting device for illuminating a tool and/or a treatment site, and with a cooling media dispensing device for dispensing at least one cooling medium onto the tool and/or treatment site.

BACKGROUND

Medical treatment devices, in particular dental treatment devices having a drive for driving a tool, a light-emitting device for illuminating (e.g., emitting light onto or generally toward) the tool and/or the treatment site, and a cooling media dispensing device for dispensing at least one cooling medium onto the tool and/or the treatment site are known, e.g., see German patent DE 195 11 262 C1.

A liquid, e.g., water, and a compressed gas, e.g., compressed air, are often used as the cooling media. By delivering the cooling media under pressure into a region above the treatment site, and the media's impact on the treatment site and/or tool and bouncing off and spraying from the treatment site and/or tool, curtain of mist typically shrouds the treatment site. Such a curtain of mist interferes with the light emitted from the light-emitting device and can prevent the light from reaching the treatment site, as by scattering, diffraction and/or absorption effects, and thereby obstructs the user's view of the treatment site.

Disclosed herein are embodiments and aspects of treatment devices that provide users with a better view of the treatment site compared to previously known devices.

SUMMARY

Some medical treatment devices (e.g., dental treatment devices) have a drive unit for driving a tool configured to act on a treatment site and be connected to the drive unit, a light-emitting device for emitting light in the direction of or onto the tool and/or the treatment site, and a cooling media dispensing device for dispensing at least one cooling medium in the direction of or onto the tool and/or the treatment site. The light-emitting device can comprise at least one optical semiconductor element, such as, for example, a light-emitting diode (LED). In addition, the treatment device can comprise a control device for alternating light emission with delivery of the at least one cooling medium.

The control device can produce a pulsed or alternating sequence of light and at least one cooling medium, such that a substantially alternating sequence of light pulses and cooling medium pulses is delivered by the treatment device. During such a chronological, alternating sequence of light and cooling medium, little or no cooling medium, e.g., little or no liquid cooling medium, is present in the air space between the treatment site and the light-emitting device while the light is illuminating the site. Such an alternating sequence of light and cooling medium can reduce the extent of any disturbance or interference with the emitted light, and in some instances, can essentially eliminate any disturbance to or interference with illumination of the treatment site and/or the tool.

The control device can comprise one or more control elements or adjusting elements that act on the light-emitting device and/or on the cooling media dispensing device. For example, the control device can be coupled to a microcontroller for controlling the control elements or adjusting elements. The control device can have a control valve, e.g., a solenoid valve positioned within in a media line for a cooling medium. Such a valve can be intermittently triggered to open or close by control signals from the microcontroller. The pulse rate of the control signals or the control valve, and a corresponding frequency of the pulsed dispensing of cooling media can be at least about 25 Hertz (Hz), and in some instances more than about 50 Hz, with about 75 Hz being but one example.

According to some embodiments, the control device is configured to emit a first control signal for providing a pulsed emission from the light, and a second control signal for providing a pulsed delivery of the at least one cooling medium. The first and the second control signals can overlap at least partially in time (e.g., the first and second control signals can be emitted in respective "on" and "open" phases simultaneously for a duration less than the duration of either the "on" phase or the "open" phase). The first control signal for pulsed delivery of the light can comprise an electrical impulse, e.g., an impulse of electric current for operating the light-emitting device. In such an embodiment, an especially accurate alternating delivery of light and cooling media can be achieved Phase-shifted emission of the first and second control signals can take into account and compensate for the inertia of the liquid cooling medium and that of the control valve which provides the pulsed delivery of the cooling medium. Inertial effects typically result in a delayed dispensing of a cooling medium pulse from the treatment device relative to the leading edge (e.g., initiation) of an "open" phase control signal pulse. By comparison, the period of time between emission of the "on" control signal for initiating a light emission and the delivery of a light pulse by the light-emitting device is much smaller. By at least partially overlapping the two control signals, delay between emitting the control signal for dispensing the cooling medium and delivery of a cooling medium pulse can be compensated for so as to reduce or eliminate any period of delay between light being emitted and cooling medium being dispensed. In other words, delivery of a cooling medium pulse to the tool and/or the treatment site is phase-shifted in relation to the delivery of the second control signal for the dispensing the cooling medium, and this phase-shift can be compensated for as described above.

The control device can also have an electric or electronic switching element for pulsing an electric power supply (e.g., an electric current) to the light-emitting device. The pulse rate of the lighting device is preferably above the "flicker frequency" of human eyesight and is preferably at least about 25 Hz, such as higher than about 50 Hz, so as to provide a user with the impression that light is continuously emitted.

According to some embodiments, the control device also has at least one adjusting element for adjusting one or more of the duration of light emission by the light-emitting device, the duration of dispensing the at least one cooling medium, and the degree of overlapping emission of the first control signal for pulsing the light and the second control signal for pulsing delivery of the at least one cooling medium.

Some treatment devices as disclosed herein comprise a handle element that can be held in the hand, such as a medical (e.g., a dental) handpiece or contra-angle handpiece or a gun-shaped handle piece. Disclosed treatment devices also comprise a drive unit comprising, for example, a movable shaft, entraining elements, gears, electric motors and/or motors operable by compressed gas, etc., and a power source (or a connection-member for connecting to a power source) for supplying power to the drive unit, the lighting device and the control device. Treatment devices can also comprise one or more connections to one or more respective media sources (e.g., a water supply and a compressed air source, and corresponding supply lines). The control device can be entirely within the handle element, or partially within the handle element. For example, a microcontroller and user-operable switching or adjusting elements can be located outside of the handle element, such as in an independent control unit.

Disclosed lighting devices can comprise one or more light-emitting diodes which are connected to an electric and/or electronic control unit for supplying electric power to the light-emitting diodes. Such control units can comprise a transformer for providing appropriate voltage levels to the light-emitting diode. The control unit is preferably configured as part of the control device. The light-emitting diodes can be provided on or within the handle element, e.g., around the tool, and/or positioned separately from the handle element, e.g., in an overhead lamp or in a separate lighting unit that can be introduced into the oral cavity. Some lighting devices comprising a first lighting unit on the handle element and a second separate lighting unit can provide especially good visibility for the user when combined with a pulsed light emission from both lighting units.

Tools, which can be set in motion by the drive unit, can comprise, for example, a rotary drill, a vibrating probe or a file that executes a lifting motion. The drive unit can comprise corresponding elements which provide the driving motion required by the respective tool, if necessary, as by converting one driving motion into another.

Cooling media dispensing devices can comprise one or more lines, which are connected to one or more respective cooling medium sources and pass through at least a portion of the treatment device. At respective ends facing the treatment site, the lines can open into and/or define dispensing openings of the treatment device, e.g., the lines can open into openings in the outer shell of the handle element. The cooling medium can be delivered to the tool and/or the treatment site through the dispensing openings and nozzles optionally connected thereto. The cooling media dispensing device can comprise a pressure regulating valve for regulating a line pressure of the at least one cooling medium, e.g., so that the at least one cooling medium flowing to an adjusting element of the control device has an essentially constant pressure. Such configurations can provide an especially reliable and constant pulse rate of the cooling medium.

According to one embodiment, several cooling media can be conveyed through the cooling media dispensing device, such that the control device provides alternating delivery of at least two of the cooling media (e.g., compressed air and water). A mixing unit can be provided for mixing the at least two cooling media, and an adjusting element provided downstream from the mixing element can provide alternating delivery of the mixed cooling media. This can be an especially space-saving embodiment since only a single shared adjusting element, e.g., a valve, is necessary for delivering two or more media.

According to another embodiment, several cooling media (or several mutually independent streams of one cooling medium) can be conveyed through separate lines of the cooling media dispensing device. The control device can be configured to provide alternating delivery of at least two of these cooling media (or cooling media streams), e.g., at least one adjusting element for alternating delivery can be assigned to each cooling medium (or cooling medium stream) so as to deliver the at least two media in an alternating or repeating sequence. Such embodiments can deliver different cooling media, e.g., compressed air and water, separately and in different cycles, e.g., one pulse of a first cooling medium in repeating or alternating sequence with a light pulse. In this manner, a pulse of the first cooling medium can be delivered with or independently of every second, third or n-th pulse of the second cooling medium. Two or more streams of one cooling medium can be delivered in a similar fashion. Such periodic or intermittent delivery of cooling streams can provide a good view of the treatment site to a user and, for example, adequate cooling of the treatment site, as well as efficient rinsing of the treatment site aided by the delivery of the second cooling medium stream. Separate dispensing openings corresponding to each cooling medium, or, after mixing of the cooling media or cooling media streams in a mixing unit, shared dispensing openings, can convey the cooling media or plural medium streams.

Plural cooling media can be conveyed through the cooling media dispensing device. At least one cooling medium can be delivered continuously to the tool and/or the treatment site, and at least one other cooling medium can be delivered in alternating sequence with the light. The continuously delivered cooling medium can comprise a majority portion of a compressed gas (e.g., compressed air) and the other, alternating (or pulsed) cooling medium can comprise a majority portion of a liquid (e.g., water). One advantage of such an embodiment is that the continuous cooling medium (e.g., compressed air) can rapidly blow away or remove the pulsed cooling medium (e.g., water) from the treatment site, the tool and the space above the treatment site, so as to provide a clear path for emitted light pulses and the user's view of the treatment site or the tool. Separate dispensing openings can facilitate these and other advantages.

Medical treatment methods, such as dental treatment methods, are also disclosed. Such methods can comprise delivering light and at least one cooling medium to a tool and/or a treatment site in alternating sequence (e.g, a light pulse and a cooling medium pulse can be delivered in alternating sequence). Two different cooling media can be delivered by the treatment device in such methods. For example, one cooling medium, e.g, a compressed gas, such as compressed air) can be delivered continuously, while another cooling medium, e.g., liquid water, can be delivered in alternating sequence with the light.

These and other principles are explained in greater detail below in connection with but one of many possible embodiments and with reference to the accompanying drawings.

DETAILED DESCRIPTION

Figure 1:
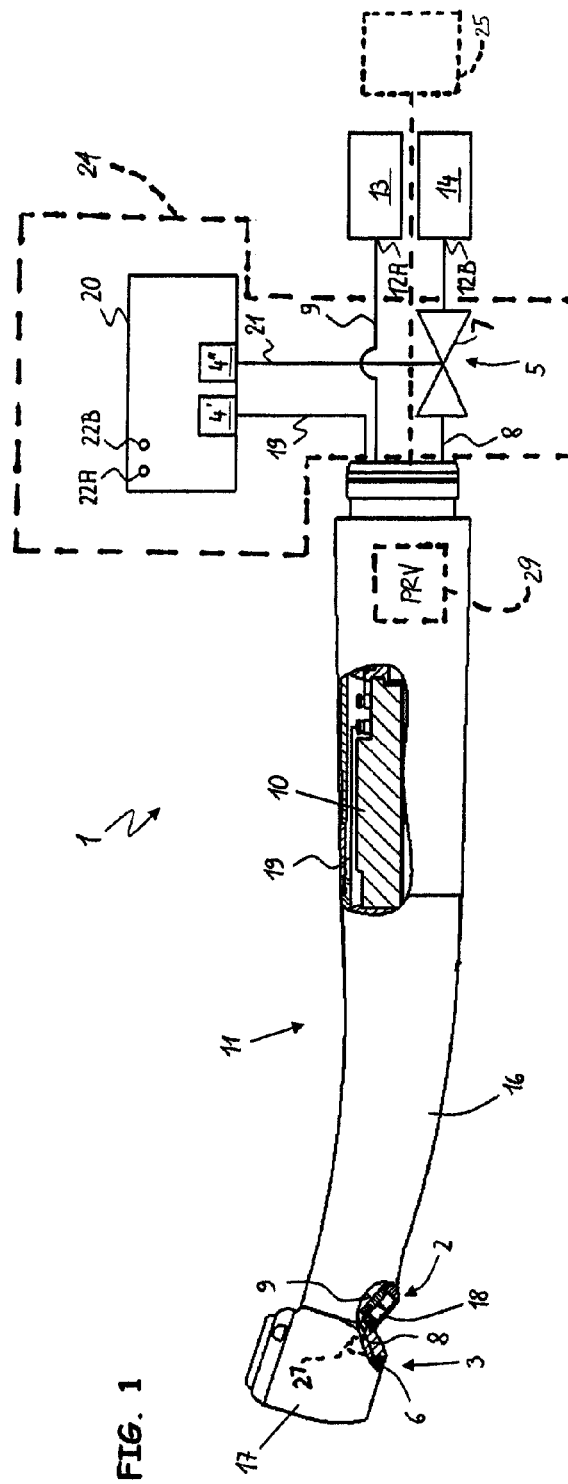
FIG. 1 shows a treatment device having a dental contra-angle handpiece, a connection to a first cooling medium source, a connection to a second cooling medium source and a control device for alternating light emissions and delivery of a cooling medium.

The treatment device 1 illustrated in FIG.1 comprises a handle element 11 that can be gripped with one hand, connections 12A, 12B to a compressed air source 13 and a water source 14, respectively, a light-emitting device 2, a cooling media dispensing device 3 and a control device 24 for alternating delivery of light and at least one cooling medium.

The illustrated handle element 11 comprises a dental contra-angle handpiece with a curved or angled handle section 16 and a head section 17 oriented at an angle to the former. In the head section 17, a tool receptacle, into which a tool can be detachably inserted, is provided. A tool release mechanism is also provided for releasing the tool from the tool receptacle. A working movement of the tool receptacle is induced by a drive unit 25 comprising, for example, a rotor driven by compressed air, an oscillating axle or rotary shafts and gearwheels. It is possible for the handle element to have other known configurations, such as, for example, a straight handpiece or a pistol-shaped handle element. The handle element 11 comprises known intermediate pieces, connecting pieces, couplings, adapters, hose connections, etc., that do or can support, connect couple, engage, etc. the tool.

As shown in FIG. 1, a water line 8 and an air line 9 can extend from the connections 12A, 12B through the treatment device 1 (e.g., through a supply tube and the handle element 11) to the media dispensing openings (only one opening 6 is shown in FIG. 1) which are positioned adjacent the tool and/or adjacent the tool receptacle opening through which the tool can extend into the tool receptacle. One or more cooling media can flow from the media dispensing openings (or nozzles or guide elements) into a region above the treatment site, a region adjacent the tool and toward the treatment site and the tool. The illustrated media lines 8, 9 and the media dispensing openings 6 comprise a portion of the cooling media dispensing device 3.

The light-emitting device 2 comprises a light source 18 for emitting visible light. The light source can comprise at least one optical semiconductor element, e.g., at least one light-emitting diode (LED). An electronic controller 10 can supply the light source 18 with electric power required to operate the light source 18 and comprises electric lines 19 for connecting the light source 18 and the electronic controller 10 to an electric power source. If the electric power source is positioned outside of the treatment device, one or more other connections can be provided for connecting the electrically powered devices of the treatment device to the electric current source.

The at least one LED can be positioned within a hermetically sealed capsule or enclosure, which can comprise metal, glass, plastic or synthetic resin components, allowing the handle element 11 to be cleaned with the LED remaining in place. This is particularly desirable so the handpiece can be disinfected or sterilized (e.g., in an autoclave). The capsule housing the LED can be arranged in an opening in the outer shell of the handle element 11, such that emitted light is generally directed onto or toward the tool and/or the treatment site. Alternatively, the light-emitting device 2 can comprise an optical light guide for directing the light generated by an LED toward the tool and/or the treatment site (or directly onto the tool and/or treatment site).

The electronic controller 10, e.g., when it is located in the handle element 11, can be hermetically encapsulated in a housing or other enclosure to protect it from soiling, water vapor or aggressive cleaning agents. Such a housing can comprise a metal, plastic or synthetic resin housing or a casting comprising a curable casting material.

The controller 24 for alternating delivery of light and at least one cooling medium can comprise a control unit 20, in which one or more electronic switching elements or circuits 4', 4" are located. The controller 24 can also comprise one or more mechanical adjusting elements 5, as well as electric lines 19, 21 for connecting the circuits 4', 4" to the adjusting elements 5 and/or for relaying electric control signals.

A first circuit 4' provided in the control unit 20 controls light emissions from the light-emitting device 2. During alternating delivery of light and coolant, the circuit 4' turns the power supply of the light-emitting device 2 on and off, preferably periodically, so the light source 18 is alternately supplied with power (on) and removed from power (off), so light (or a light pulse) is alternatingly emitted (or strobed). The switching frequency can be at least about 25 Hz, such as more than about 50 Hz, with about 75 Hz being but one example of many possible switching frequencies.

Instead of the circuit 4' being positioned within the control unit 20, the circuit can be integrated into the electronic controller 10 in the handle element 11. Some embodiments locate the electronic controller 10 in the control unit 20.

The second circuit 4" in the control unit 20 controls delivery of the cooling liquid, e.g., a spray of water. Such a spray of water can be dispensed to the treatment site and/or the tool in an alternating sequence with the pulsed light. The second circuit 4" can be coupled by way of the line 21 to an adjusting element 5 positioned within the water line 8. The adjusting element 5 can be configured as a control valve 7, such as a solenoid valve. The second circuit 4" can send control signals to the adjusting element 5 to open or close it, so as to deliver water substantially only when the light-emitting device 2 is not emitting light.

According to the embodiment illustrated in FIG. 1, the adjusting element 5 is spaced from the opening 6 from which the water is dispensed. The adjusting element 5 can be positioned in the handle element 11, e.g., in the area of the electronic controller 10, or outside of the handle element 11, e.g., in a coupling connected to the handle element 11.

Because of the inertia of the control valve 7 and the water column in the water line 8 between the control valve 7 and the media dispensing opening 6, there typically is a delay in time between the act of triggering the control valve 7 by the second circuit 4" and the actual delivery of water to the opening 6. To compensate for such a delay, and thereby ensure an accurate (e.g., an evenly distributed and periodic) alternating sequence of light and water delivery, the control device 24 can be configured to at least partially overlap a first control signal for pulsing light with a second control signal for pulsing the at least one cooling medium. For example, electric power (e.g., current) used to operate the light-emitting device can serve as the first control signal for pulsing the light. In such embodiments, the control device 24 sends electric power to the light source 18 and an "open" control signal to the control valve 7 (e.g., for opening the control valve 7) simultaneously for at least a short duration.

Such a treatment device 1 can deliver water (or water pulses) and light (or light pulses) in an alternating sequence. Compressed air can be conveyed through the handle element 11 via the line 9 and delivered continuously generally toward the tool, the treatment site and the region above the treatment site during operation of the handle element 11 by way of one or more compressed air dispensing openings (not shown in FIG. 1). Such separate dispensing openings for compressed air can be positioned on the head section 17 of the handle element 11 or on an adjacent portion of the handle section 16. The air dispensing openings can be positioned near the water-dispensing openings 6 so that a continuous flow of air blows away water (e.g., a mist) in the region above the treatment site, providing a better view of the treatment site to the user.

Alternatively, the compressed air and the water can be dispensed from the same media-dispensing openings 6. For example, a dispensing device, e.g., a spray plate, can be provided around the tool or the tool receptacle opening, for example, with both the water line 8 and the air line 9 opening into the dispensing device. A mixing unit or mixing chamber can be provided in the dispensing device. Such a mixing unit can mix the water and the compressed air together before they flow out of the openings of the dispensing device as a water-air mixture, or spray. For example, a joint line segment in the dispensing device, through which the water and the compressed air can flow jointly, can also serve as a mixing chamber 27. A continuously flowing stream of compressed air can flow through the line 9 into the spray plate, and water pulses can be intermittently introduced (e.g., in an alternating sequence) with the light pulses. In such an embodiment, the mixing chamber for the two cooling media can be positioned downstream from the adjusting element 5 for the water.

The control unit 20 can comprise additional electric or electronic circuits or control circuits, memories, displays, adjusting elements, etc., for operating the treatment device 1, the drive unit, e.g, an electric motor, and/or the handle element 11. Different operating conditions having different parameters, fixed parameters or parameters that can be varied by an adjusting element 22A, e.g., a maximum rotational speed, a maximum torque, can be stored in a memory. The duration of light emission by the light-emitting device 2 and/or a duration of cooling medium dispensing and/or the degree of overlap between control signals the light and delivery of the at least one cooling medium can be adjusted by another adjusting element 22B.

Figure 2:
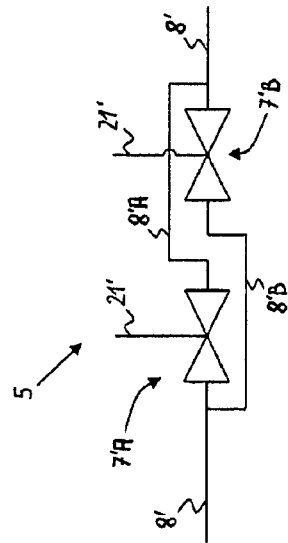
FIG. 2 shows a schematic illustration of an alternative embodiment of an adjusting element for alternating delivery of a cooling medium.

FIG. 2 schematically shows an alternative embodiment of an adjusting element positioned within the water line. In FIG. 2, the water line 8' splits into two parallel branches 8'A and 8'B, dividing a flow of water into two partial flows. Positioned in each of the line branches 8'A, 8'B are respective valves 7'A, 7'B, e.g., a solenoid valve, that can be controlled by the circuit 4" via the lines 21' (see FIG. 1). The valves 7'A, 7'B can be fluidly coupled in parallel, such that a substream of coolant flows through each of the valves 7'A, 7'B. Although fluidly coupled in parallel, the valves 7'A, 7'B are physically positioned in substantially end-to-end relation to each other, e.g., in serial or sequential spatial arrangement. Downstream from the valves 7'A, 7'B, the line branches 8'A, 8'B can recombine in a line 8' so as to recombine the substreams in a common cooling medium stream.

Optionally, a pressure regulating valve 29 can be provided such that pressures in line(s) downstream of the valve are kept substantially constant or allowed to vary only as desired.

One advantage of the configuration shown in FIG. 2 is the relatively smaller diameter provided. For a given flow rate of cooling medium, a smaller diameter can usually be achieved using two valves, as shown, rather than a single valve. In other words, a single valve capable of accommodating the flow rate of the combined streams is typically larger in diameter than a valve being capable of accommodating about one-half of the flow rate as provided by the configuration shown in FIG. 2.

The following claims are not limited to the embodiments described and illustrated here but instead cover all embodiments which apply or comprise the appropriate function and/or principle described. In addition, features of the embodiments illustrated and described here can be combined with one another.

What is claimed is:

1. A medical treatment device, comprising:
   a drive unit configured to drive a tool that is connectable to the drive unit and being configured to act on a treatment site;
   a light-emitting device configured to emit visible light onto one or both of the tool and the treatment site;
   a cooling media dispensing device configured to dispense at least one cooling medium from the medical treatment device onto one or both of the tool and the treatment site; and
   a controller configured to control the light-emitting device and the cooling media dispensing device to operate alternatingly with respect to each other, thereby causing visible light from the light-emitting device to be emitted alternatingly with dispensing of the at least one cooling medium from the dispensing device,
   wherein a pulse rate of the light-emitting device controlled by the controller is at least about 25 Hz, so as to provide the user of the medical treatment device with the impression that the visible light is continuously emitted.

2. The medical treatment device of claim 1, wherein the cooling media dispensing device is configured to dispense a plurality of cooling media, the treatment device further comprising a mixing unit configured to mix at least a first cooling medium with a second cooling medium, and wherein the cooling media dispensing device comprises an adjusting element connected to and positioned downstream of the mixing unit, wherein the controller is configured to control the adjusting element to operate alternatingly with the light-emitting device such that when the adjusting element is operated, a mix of the first cooling medium and the second cooling medium is dispensed from the adjusting element.

3. The medical treatment device of claim 1, wherein the cooling media dispensing device is configured to convey a plurality of cooling media or a plurality of independent streams of a cooling medium, the controller is configured to control the dispensing device to dispense at least two of the plurality of cooling media or plurality of cooling medium streams in an alternating sequence with the visible light emission, the treatment device further comprising at least one adjusting element corresponding to each cooling medium or cooling medium stream and being so configured as to pulse the respective cooling medium or stream in alternation with the visible light pulses.

4. The medical treatment device of claim 1, wherein:
   the cooling media dispensing device is configured to convey a plurality of cooling media, and
   the controller is configured to control the cooling media dispensing device to dispense at least a first cooling medium substantially continuously and to dispense at least a second cooling medium in alternation with operation of the light-emitting device.

5. The medical treatment device of claim 4, wherein:
   the first cooling medium comprises a majority portion of a compressed gas, and the second cooling medium comprises a majority portion of a liquid.

6. The medical treatment device of claim 4, further comprising:
   a mixing unit for mixing at least the second cooling medium and the first cooling medium, and
   an adjusting element positioned upstream from the mixing unit for intermittently dispensing the second cooling medium dispensed in alternation with operation of the light-emitting device.

7. The medical treatment device of claim 3, further comprising at least one dispensing opening corresponding to each cooling medium.

8. The medical treatment device of claim 4, further comprising at least one dispensing opening corresponding to each cooling medium.

9. The medical treatment device of claim 1, wherein the cooling medium dispensing device comprises at least one media line, and the controller comprises at least one controllable adjusting element positioned at least partially within the media line, the adjusting element comprising a control valve.

10. The medical treatment device of claim 9, further comprising:
a plurality of control valves fluidicly coupled in parallel such that first and second substreams of at least one of the at least one cooling medium can flow through respective first and second control valves in parallel, and wherein at least the first and second control valves are arranged in substantially end-to-end relation to each other.

11. The medical treatment device of claim 1, wherein the controller comprises a switching element for pulsing an electric power supply to the light-emitting device.

12. The medical treatment device of claim 1, wherein the controller is configured to temporally overlap emission of a first control signal for pulsing the light and a second control signal for pulsing delivery of the at least one cooling medium.

13. The medical treatment device of claim 1, wherein the cooling media dispensing device comprises a pressure regulating valve for regulating a line pressure of at least one of the at least one cooling medium such that cooling medium downstream of the valve has a substantially constant line pressure.

14. The medical treatment device of claim 1, wherein the treatment device comprises a handle that can be gripped by a user's hand, and wherein the light-emitting device is coupled to the handle element.

15. The medical treatment device of claim 1, wherein the controller comprises at least one adjusting element configured to be operated by a user and to adjust one or more of a duration of visible light emission by the light-emitting device, a duration of delivery of the at least one cooling medium, and a degree of temporal overlap of a first control signal for pulsing the visible light and a second control signal for pulsing delivery of the at least one cooling medium.

16. The medical treatment device of claim 1, wherein the light-emitting device comprises at least one optical semiconductor element.

17. A method of illuminating a medical treatment site, with a visible light, comprising:
driving a tool of a medical handpiece with a drive unit, wherein the tool is configured to act on a medical treatment site;
pulsing a visible light source of the handpiece so as to intermittently illuminate at least one of the tool, a treatment site and a region adjacent a treatment site with visible light emitted from the light source; and
dispensing at least one cooling medium from the handpiece in substantial alternation with pulsing the visible light source,
wherein a pulse rate of the light source is at least about 25 Hz or higher than about 50 Hz, so as to provide the user of the medical handpiece with the impression that the visible light is continuously emitted.

18. The method of claim 17, wherein the at least one cooling medium comprises at least a first cooling medium and a second cooling medium, further comprising dispensing the first cooling medium independent of the dispensing of the second cooling medium that occurs substantially alternatingly with the pulsing of the visible light source.

19. A medical treatment device comprising:
a handle element;
a drive unit positioned within the handle element and being configured to drive a tool configured to act on a treatment site;
a light-emitting device configured to emit visible light from the handle element so as to illuminate at least one of the tool and the treatment site, wherein the light-emitting device comprises a light source which is arranged at the handle element;
a cooling medium dispenser configured to intermittently dispense at least one cooling medium from the handpiece toward at least one of the tool, the treatment site and a region adjacent the treatment site; and
a controller configured to control the light-emitting device to emit visible light, and to control the dispenser to dispense the at least one cooling medium substantially alternatingly with respect to each other such that pulses of visible light are alternated with pulses of the at least one cooling medium.

20. The medical treatment device of claim 19, wherein the cooling medium dispenser comprises an adjusting element, and wherein the controller comprises a first circuit for conveying a first control signal for pulsing the light-emitting device, and a second circuit for conveying a second control signal for opening and closing the adjusting element so as to intermittently dispense the at least one cooling medium.

21. The medical treatment device of claim 19, wherein the cooling medium dispenser is configured to dispense a plurality of cooling media and wherein the handle element further comprises a mixing unit configured to mix at least a first cooling medium which is dispensed substantially alternatingly with the visible light with a second cooling medium.

22. The medical treatment device of claim 21, wherein the cooling medium dispenser is configured to dispense the second cooling medium according to one of: substantially alternatingly with the visible light and continuously.

* * * * *